United States Patent [19]

Koster

[11] Patent Number: 5,198,540
[45] Date of Patent: Mar. 30, 1993

[54] PROCESS FOR THE PREPARATION OF OLIGONUCLEOTIDES IN SOLUTION

[76] Inventor: Hubert Koster, 1640 Monument St., Concord, Mass. 01742

[21] Appl. No.: 368,965

[22] PCT Filed: Oct. 27, 1983

[86] PCT No.: PCT/EP83/00281

§ 371 Date: Jun. 25, 1984

§ 102(e) Date: Jun. 25, 1984

Related U.S. Application Data

[63] Continuation of Ser. No. 861,654, May 5, 1986, abandoned, which is a continuation of Ser. No. 624,672, Jun. 25, 1984, abandoned.

[30] Foreign Application Priority Data

Oct. 28, 1982 [DE] Fed. Rep. of Germany ....... 3239887

[51] Int. Cl.$^5$ ................ C07H 21/00; C07C 69/74
[52] U.S. Cl. ................ 536/25.3; 536/25.31; 536/25.33; 560/1
[58] Field of Search ................ 536/27–29

[56] References Cited

U.S. PATENT DOCUMENTS

| | | | |
|---|---|---|---|
| 4,415,732 | 11/1983 | Caruthers et al. | 536/27 |
| 4,417,046 | 11/1983 | Hsiung | 536/27 |
| 4,458,066 | 7/1984 | Caruthers et al. | 536/27 |

OTHER PUBLICATIONS

Miller et al., vol. 18 (23), pp. 5134–5143, 1979.
Burgers et al, Tetrahedron Lett. 40 pp. 3835–3838 (1978).
Nemer et al, Tetrahedron Letters, vol. 21, pp. 4153–4154 (1980).
Gough et al, 22 (42), pp. 4177–4180 (1981).
Sinha et al., Tett. Lett., vol. 24 (9), pp. 877–880, 1983.
W. Gohring and G. Jung, Liebigs. Ann. Chem., 1975, pp. 1776–1780.
W. Gohring and G. Jung, Liebings. Ann. Chem., 1975, pp. 1781–1789.
W. Gohring and G. Jung, Liebigs. Ann. Chem., 1975, pp. 1765–1775.
M. M. Shemyakin et al., *Tetrahedron Letters, No. 27 2323–2327 (1965)*.
N. Mutter and E. Bayer, *Angew. Chem., 86:101–102 (1974)*.
Hagenmaier, Hoppe-Seyler's Z. Physiol. Chem., 356, 777–785 (1975).
Agarwal et al., Chem. Abstr., 90:87782m (1979).

*Primary Examiner*—Johnnie R. Brown
*Assistant Examiner*—L. Eric Crane
*Attorney, Agent, or Firm*—Hamilton, Brook, Smith & Reynolds

[57] ABSTRACT

Process for the preparation of oligonucleotides by successive linking of individual or several nucleoside and-/or nucleotide units in a homogeneous phase system using a bi-, tri- or tetra-functional carrier molecule of the general formula $Sp(X)_n$, wherein X is a reactive group which is compatible from the point of view of nucleotide chemistry and n is an integer from 2 to 4, the sequence $SP(X-N^1-N^2 \ldots N^m)_n$ being built up stepwise on the carrier molecule and the oligonucleotide of the formula $N^1-N^2 \ldots N^m$ subsequently being released.

8 Claims, 10 Drawing Sheets

PROCESS FOR THE PREPARATION OF OLIGONUCLEOTIDES IN SOLUTION

This is a continuation of co-pending application Ser. No. 06/861,654 filed on May 5, 1986 which is a file wrapper continuation of Ser. No. 06/624,672 Jun. 25, 1984, both now abandoned.

The invention relates to a process for the preparation of oligonucleotides by successive linking of individual or several nucleotide units in a homogeneous phase system, each linking step being followed by working up of the reaction mixture by chromatography.

Various processes have been disclosed as a result of the importance of synthetic oligonucleotides for isolating genetic material. According to the most recent state of the art, these processes are carried out either by the phosphate triester method or by the phosphite triester method, the use of polymeric carriers as the heterogeneous phase having proved to be particularly advantageous. The use of polymeric carriers serves, in particular, to simplify the working up of the reaction mixtures after the condensation steps by replacing expensive chromatographic separation processes with filtrations. Moreover, automation of the individual reaction steps is also possible. However, these processes have the disadvantage that oligonucleotides can thereby be isolated only in relatively small amounts.

The invention relates to a process of the abovementioned type, with which relatively large amounts of oligonucleotides having a defined sequence can be obtained. It is possible to prepare not only the naturally occurring oligo-diesters, but also analogous oligomers, such as oligo-triesters or oligophosphonates.

The process according to the invention is characterized by the following reaction steps:

a) reaction of a polyfunctional carrier molecule, which is soluble in the particular reaction mixture, of the general formula I $$\text{Sp}(X)_n \quad (I)$$

in which n denotes an integer from 2 to 4, X is a reactive group which is compatible from the point of view of nucleotide chemistry and Sp is an optionally branched alkylene polyalkylene group with 1–30 carbon atoms, an arylene or polyarylene group with 1–10 aryl groups, a polyaralkylene group with 1–10 aryl groups, a polyaralkylene group with 2–100 aralkylene units, polyesters, polysiloxanes or polyamides with a molecular weight of up to 40,000, optionally branched alkylenedioxy compounds with 2–6 carbon atoms or optionally partially alkylated polyalkyleneoxy compounds with a molecular weight of up to 40,000, with at least an equimolar amount, based on $-(X)_n$, of a first nucleoside or nucleotide $N^1$, b) separation and purification and, if appropriate, phosphorylation of the compound obtained in stage a, of the general formula II $$\text{Sp}(X-N^1)_n \quad (II)$$

c) reaction of the compound II obtained in stage b with at least an equimolar amount, based on $-(X-N^1)_n$, of a second nucleoside or nucleotide $N^2$, d) separation and purification and, if appropriate, phosphorylation of the compound obtained in stage c, of the general formula III $$\text{Sp}(X-N^1-N^2)_n \quad (III)$$

and e) if appropriate, further successive linking and purification and, if appropriate, phosphorylation steps to form the oligonucleotide compound of the general formula IV $$\text{Sp}(X-N^1-N^2 \ldots N^m)_n \quad (IV)$$

in which m is an integer from 3 to 50, and f) subsequent release of the oligonucleotides of the general formula V $$N^1-N^2 \ldots N^m \quad (V)$$

wherein m is as defined above.

According to a preferred embodiment of the process of the invention, carrier molecules of the general formula I in which the groups X can form a silyl ether, trityl ether or ester bond with the 3'- or 5'-hydroxyl groups of a nucleoside, nucleotide or oligonucleotide are used.

According to another advantageous embodiment of the invention, a compound in which the group Sp is an alkylene or polyalkylene group with 2–10 carbon atoms is used as the carrier molecule.

Examples of the reactive group X which are customary in nucleotide chemistry are described in Liebigs Ann. Chem. 1978, 839–853 and in Nucleic Acids Research, Symposium Series No. 7, 1980, 39–59. Typical examples are, inter alia, the following:

1. Acid halides, in particular acid chlorides and acid bromides.
2. Carboxylic acid groups, which can react with 5'-OH groups, for example in the presence of condensing agents; they can also be converted into activated trityl chloride derivatives according to the following equation:

$$-\text{COOH} + \text{Y}-\text{C}_6\text{H}_4(\text{C}_6\text{H}_5)_2\text{C}-\text{Cl} \rightarrow$$

$$-\text{CO}-\text{Y}-\text{C}_6\text{H}_4(\text{C}_6\text{H}_5)_2\text{C}-\text{Cl},$$

wherein Y=OH, SH or NH$_2$;

3. Activated ester functions of the general formula —COOR'
4. OH, SH and NH$_2$ groups.

Carrier molecules of the general formula Sp(OH)$_n$ and the corresponding thio and amino derivatives are only used directly in the process of the invention if they are to react with reactive carboxyl groups. However, they are usually employed in the form of activated compounds, which can be obtained, for example, in the following manner. a) With dicarboxylic acid anhydrides, for example succinic or adipic anhydride, according to the equation $$-\text{Sp}-\text{OH} + (\text{OC}-\text{R}-\text{CO})_2\text{O} \rightarrow$$

$$-\text{Sp}-\text{O}-\text{CO}-\text{R}-\text{COOH};$$

b) With trityl derivatives according to the equation

$$-\text{Sp}-\text{OH} + \text{HOOC}-\text{C}_6\text{H}_4(\text{C}_6\text{H}_5)_2\text{COH} \rightarrow$$

$$-\text{Sp}-\text{O}-\text{CO}-\text{C}_6\text{H}_4(\text{C}_6\text{H}_5)_2\text{C}-\text{OH} \rightarrow$$
$$\text{Sp}-\text{O}-\text{CO}-\text{C}_6\text{H}_4(\text{C}_6\text{H}_5)_2\text{C}-\text{Cl}$$

This reaction can be carried out in the presence of a condensing agent or after conversion of the acid function into an acid chloride function.

c) With dichlorosiloxanes according to the general equation wherein A is alkylene, arylene, —O— or a combination of these groups and Z is halogen.

d) With hydroxyl-substituted trityl derivatives, to form trityl ether derivatives, for example of the general formula If the corresponding thio or amino derivatives are used, the corresponding S or N compounds are formed.

In selecting the group Sp, it is particularly essential that the carrier molecule $Sp(X)_n$ and its derivatives obtained in the course of the oligonucleotide synthesis of the invention are soluble in the particular reaction medium used and can be chromatographed. Examples of typical representatives are the following: optionally branched polyalkylene groups with 2-10 carbon atoms; arylene groups, for example 1,4-phenylene groups, polyarylene groups, for example 4,4'-diphenylene or 4,4'-diphenylmethane groups, polyaralkylene groups, for example those derived from polystyrene with a molecular weight of up to 10,000, corresponding to up to 100 styrene units, polyesters, for example terephthalic acid derivatives with molecular weights up to 40,000, including non-linear polyesters, where the solubility allows this, polysiloxanes with molecular weights up to 40,000, polyamides with molecular weights up to 40,000, polyalkyleneoxy compounds, for example di- or tri-ethylene glycols; branched polyalkyleneoxy compounds can be partially alkylated, so that 2-4 free OH groups are available for reactions, alkylenedioxy compounds with preferably 2-6 carbon atoms, for example 1,4-butanediol, and branched polyalkyleneoxy compounds, for example pentaerythrol.

The groups $N^1$, $N^2$ ... $N^m$ each denote customary nucleotides, nucleosides or oligonucleotides which, if appropriate, are used or obtained in the course of the synthesis in protected form; typical examples of such protective groups can be seen from Tetrahedron 1981, pages 363-369, Liebigs Ann. Chem. 1978, 839-853, and Nucleic Acids Research, Symposium Series No. 7, 1980, 39-59.

BRIEF DESCRIPTION OF THE DRAWINGS

The process according to the invention is illustrated in more detail below with reference to the Figures.

A synthesis strategy which makes it possible preferably to separate off the desired condensation product from the starting substances and by-products forms the core of the process according to the invention. This is effected by using a carrier molecule Sp as a "purification handle", which has 2-4 functional groups on which several oligonucleotide syntheses can proceed simultaneously in the course of the process. In the Figures: X denotes a functional group, Sp denote a carrier molecule or molecule portion, $N^1$, $N^2$ ... denote nucleotide units, $R^1$ denotes H or $OCH_3$, $R^2$ denotes, for example, 4-nitrophenyl or pentachlorophenyl, $R^3$ denotes H, OH or protected OH, $R^4$ denotes a permanent phosphate-protective group, for example 2-chlorophenyl-, $R^5$ denotes a temporary phosphate-protective group, for example 2-cyanoethyl or 2,2,2-trichloroethyl, $R^6$ denotes trityl, 4-monomethoxytrityl or 4,4-dimethoxytrityl, $R^7$ denotes alkyl (with 1-20 carbon atoms), aryl, aralkyl, cycloalkyl and further-more 2-cyanoethyl or 2,2,2-trichloroethyl, $R^8$ denotes acyl, in particular acetyl, laevolinyl(sic), $\beta$-benzoylpropionyl, aroyl, in particular benzoyl, and furthermore o-nitrobenzyl, tetrahydropyranyl, met oxytetrahydropyranyl (sic), t-butyldiphenylsilyl and the like, W denotes halogen, in particular chlorine or bromine, or cyano, Z denotes halogen, in particular chlorine or bromine, cyano, $N(R^7)_2$, in particular dimethylamino; triazolyl, tetrazolyl or 3-nitro-1,2,4-triazolyl and B denotes a nucleo-base or analogs.

Figure 1:
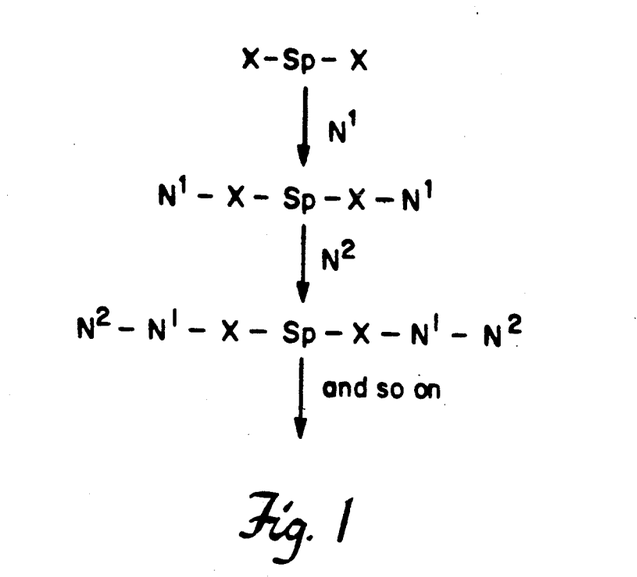

FIG. 1 shows, generally, an example for a bifunctional carrier molecule of the general formula I. The process according to the invention carried out using this carrier molecule gives a condensation product which, as the chain length progresses, differs in molecular weight to an increasing degree from the low molecular nucleotide components and by-products of the condensation reaction. This allows chromatography under mild conditions, utilizing the different sizes of the molecules.

Molecular sieves, for example based on dextran or polyamide, are suitable as the chromatography materials. Since the desired product has the highest molecular weight, it is found in the exclusion volume and is therefore eluted from the chromatography column as the first product, that is to say it is isolated first and hence in the shortest space of time. Since reversible adsorption phenomena between oligonucleotides and dextrans or polyamides are not known, in contrast to those with silica gel, the otherwise customary loss during chromatography can also be ignored.

Figure 2:
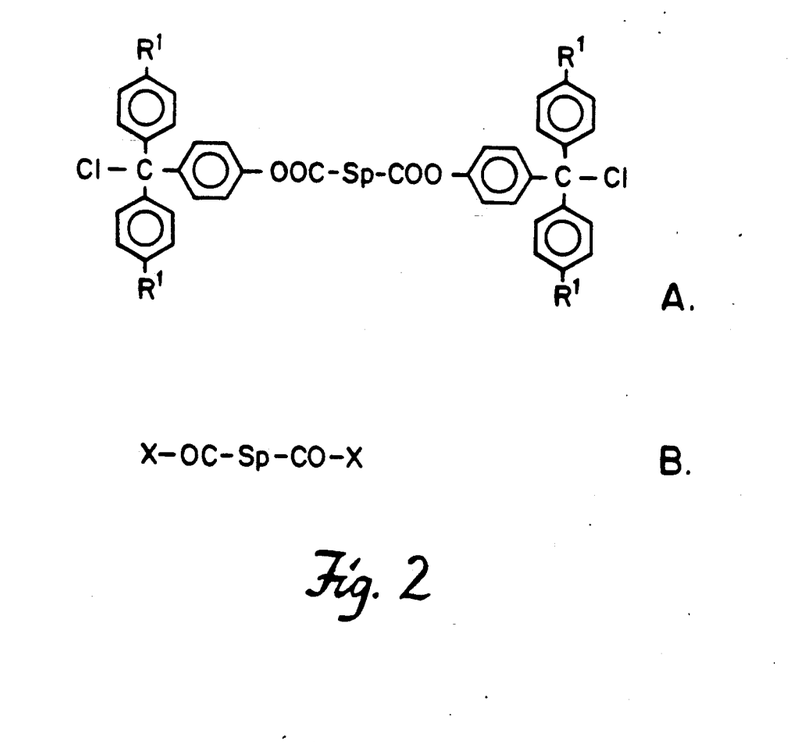

FIG. 2 shows two possibilities, in principle, of binding a bifunctional carrier molecule to the particular first nucleotide unit. Type A shows two trityl chloride groups bridged with one another via the carrier molecule, and type B shows two carboxyl groups bridged via the carrier molecule. The use of carrier molecules of type A or type B depends on the oligonucleotide synthesis strategy to be adopted and is illustrated in more detail below with the aid of FIGS. 3-8.

Figure 3:
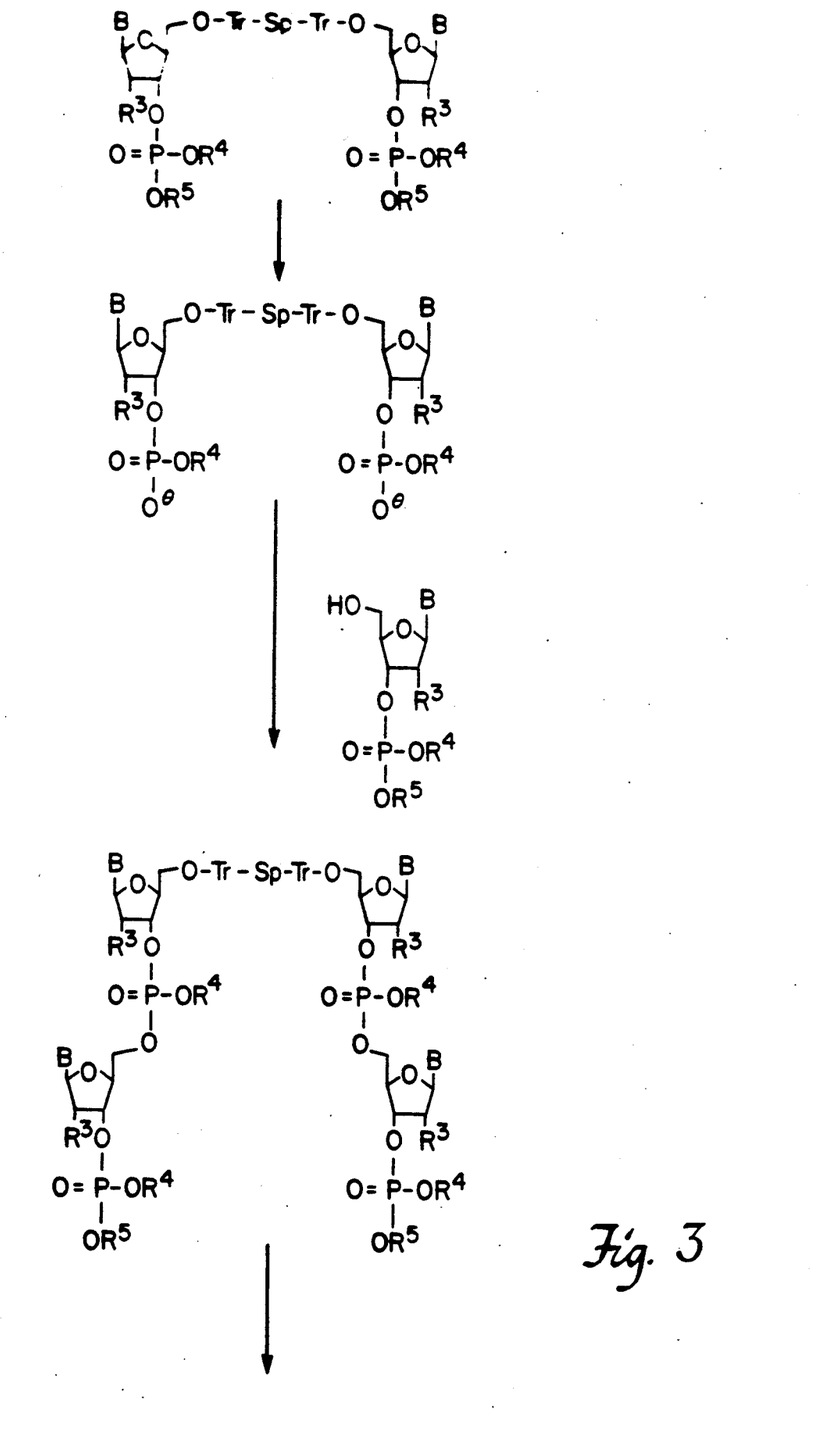

FIG. 3 shows the synthesis of an oligonucleotide after conception of the triester, using the carrier molecule of type A. The macromolecular trityl chloride is reacted with a nucleoside 3'-phosphoric acid triester, $R^4$ as a rule being 2- or 4-chlorophenyl and $R^5$ being 2-cyanoethyl or 2,2,2-trichloroethyl. After the tritylation, the temporary phosphate-protective group $R^5$ is split off, and in particular, in the case of 2-cyanoethyl, by reaction with triethylamine/pyridine or, in the case of 2,2,2-trichloroethyl, with acetylacetone/zinc, triisopropylbenzenesulfonic acid or toluenesulfonic acid/zinc or, preferably, with zinc/coreagent, where, according to experience, anthranilic acid, pyridine-2-carboxylic acid, dithioerithrol or dithiothreitol can be used. Chain lengthening is then effected with the resulting diester the phosphate component and with a nucleoside 3'-triester as the OH component, using condensing agents such as, for example, mesitylenesulfonyl-3-nitro-1,2,4-triazole (MSNT). The resulting completely protected product is purified by molecular sieve chromatography; the protective group $R^5$ is then split off and another chain lengthening step follows.

Figure 4:
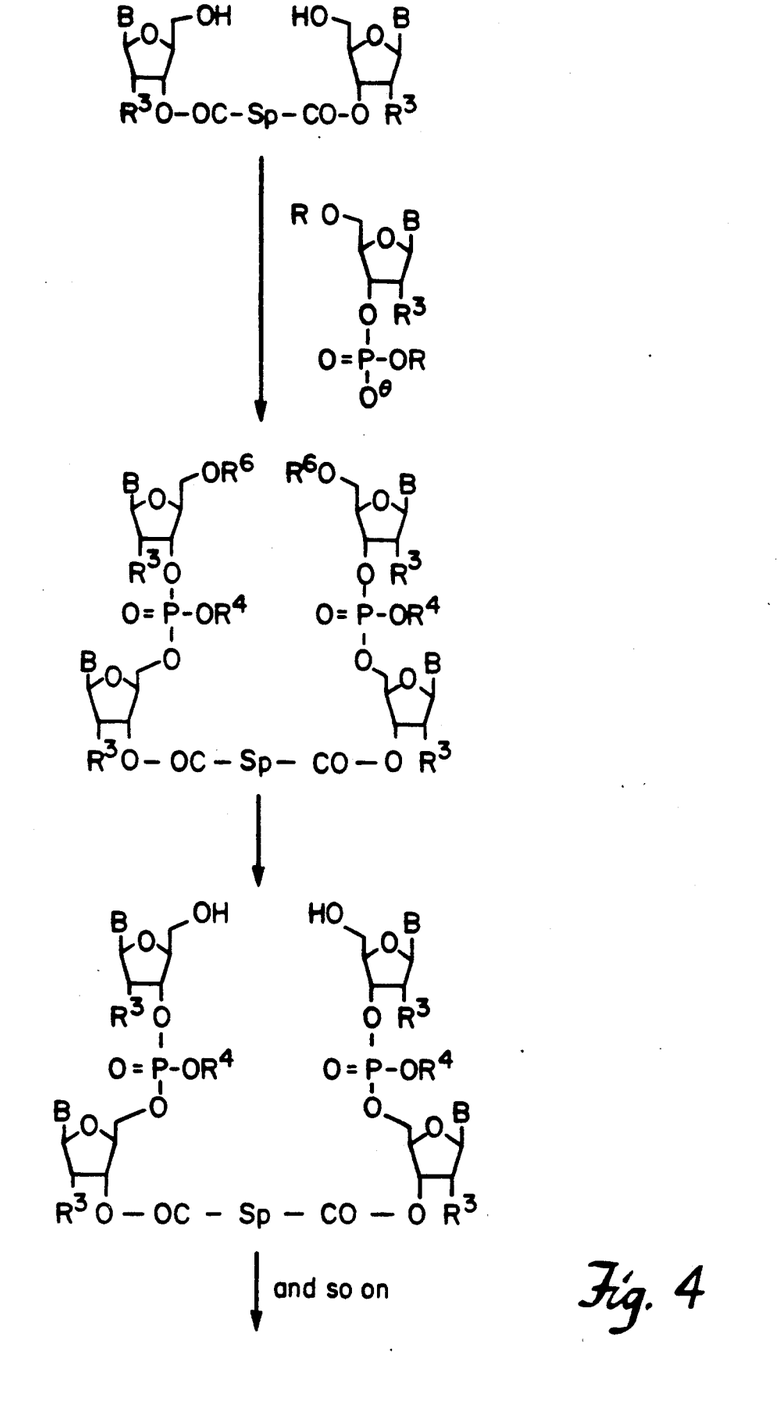

The use of the carrier molecule of type B in the triester synthesis is shown in FIG. 4. In this case, the nucleoside is coupled to the spacer molecule via the 3'-OH group in an ester-like bond and serves as the OH component. This is reacted with a 5'-tritylated 3'-nucleoside diester using a condensing agent, for example MSNT, to give the completely protected oligotriester. The product is purified by molecular sieve chromatography and splitting off of the 5'-trityl group, using either a protic acid or a Lewis acid, such as $ZnBr_2$, or a dialkyl-aluminum chloride.

Figure 5:
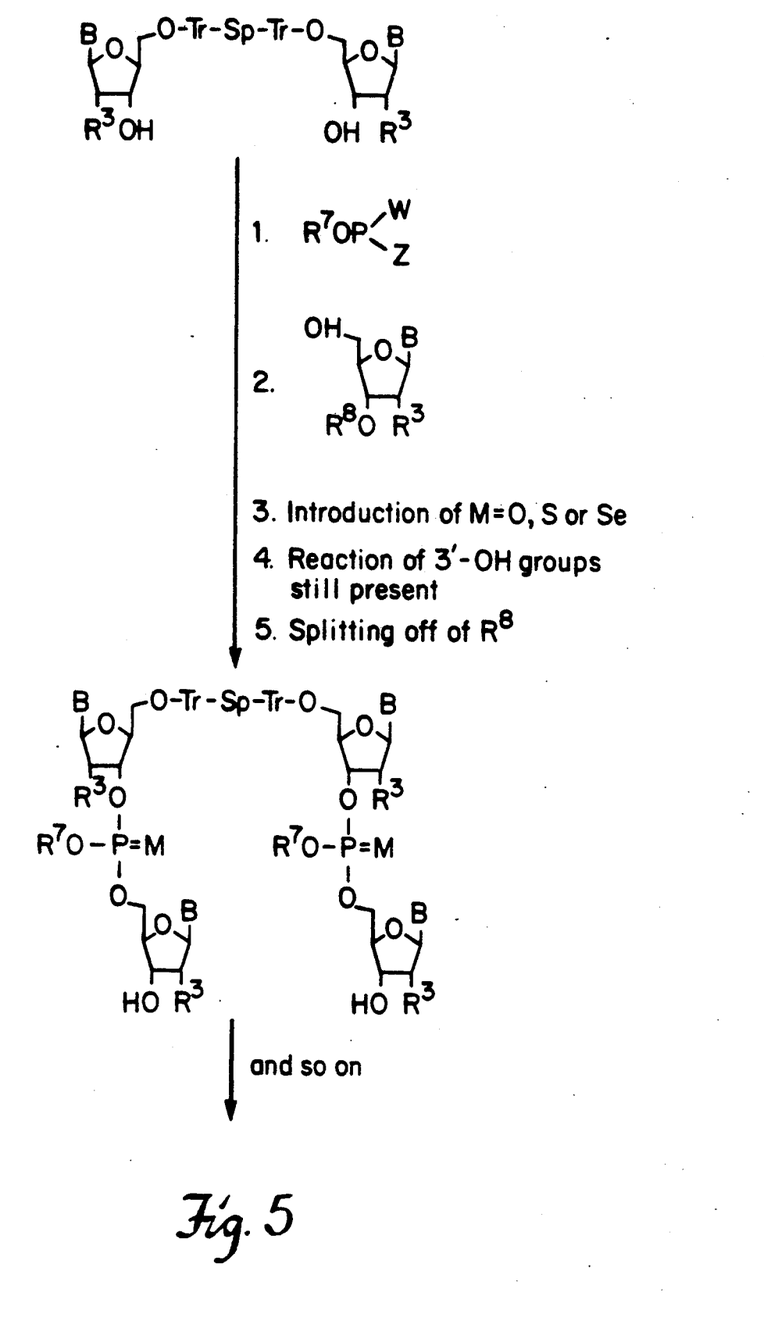

FIG. 5 shows the use of the carrier molecule of type A in the phosphite triester synthesis. Chain lengthening is started by reacting the 3'-OH group of the nucleoside bound to the carrier molecule with a protected activated phosphite in a first step, and reacting the remaining activated function with the 5'-OH group with the second nucleoside in a second step. This is now followed by introduction of O, S or Se, conversion of 3'-OH groups still present by reaction with, for example, acetic anhydride or phenyl isocyanate and subsequent splitting off of $R^8$, if necessary. The use of a 3'-OH-protective group ($R^8$) can be dispensed with if the reaction is carried out by a suitable procedure, since the regio-selectivity greatly favors the primary OH group. Other chain lengthening steps can follow.

Figure 6:
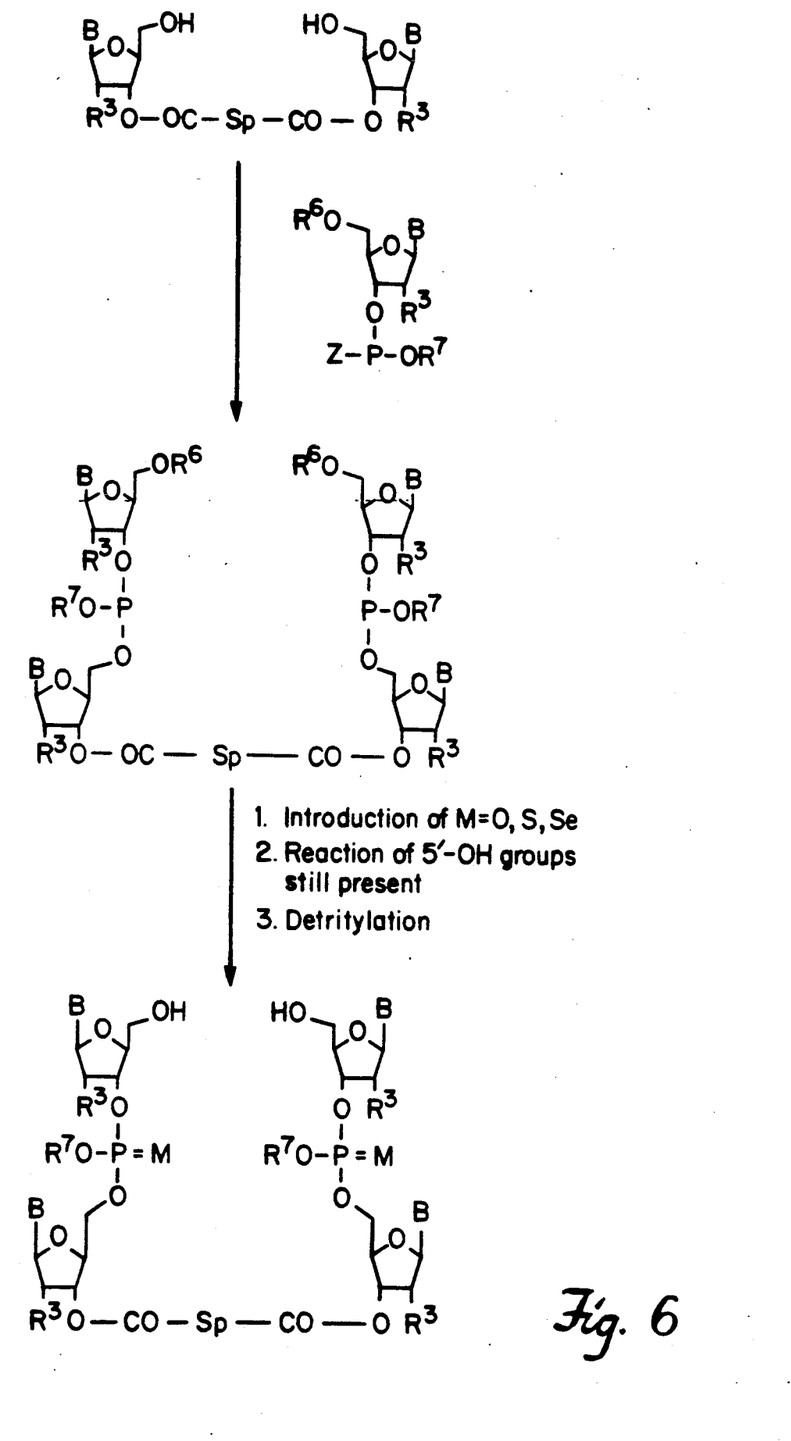

FIG. 6 shows an example of the use of the carrier molecule of type B in the phosphite triester synthesis. In this case, the nucleoside is anchored to the carrier molecule via the 3'-OH group, so that the 5'-OH group is available for chain lengthening. The chain lengthening is started by reaction with a 5'-tritylated nucleoside monochloridite. After coupling of the two nucleosides, O, S or Se is introduced, 5'-OH groups still present are converted by reaction with, for example, acetic anhydride or phenylisocyanate and detritylation is carried out with the aid of a protic acid or a Lewis acid, such as $ZnBr_2$, or a dialkyl-aluminum chloride. Further chain lengthening steps can follow.

Figure 7:
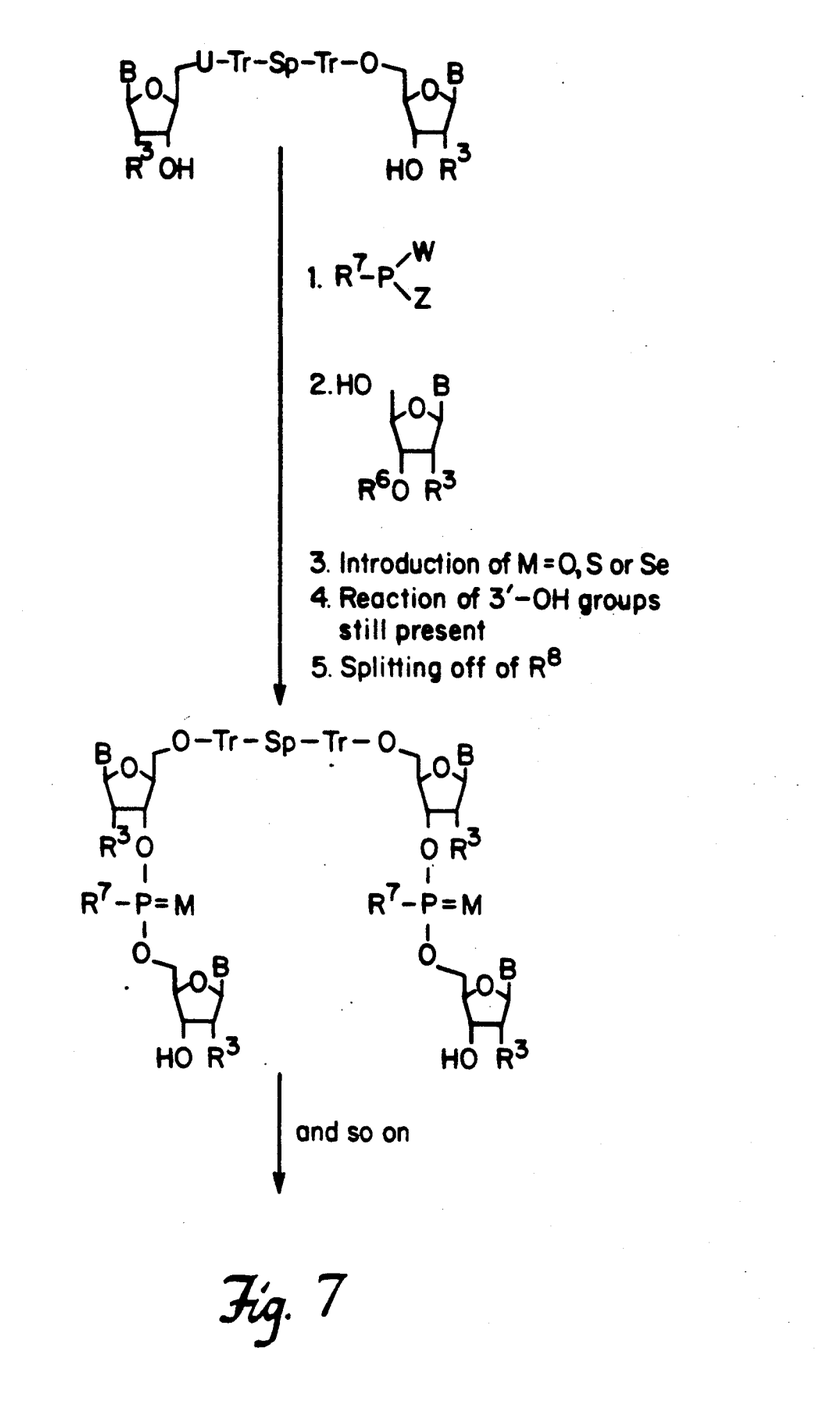
Figure 8:
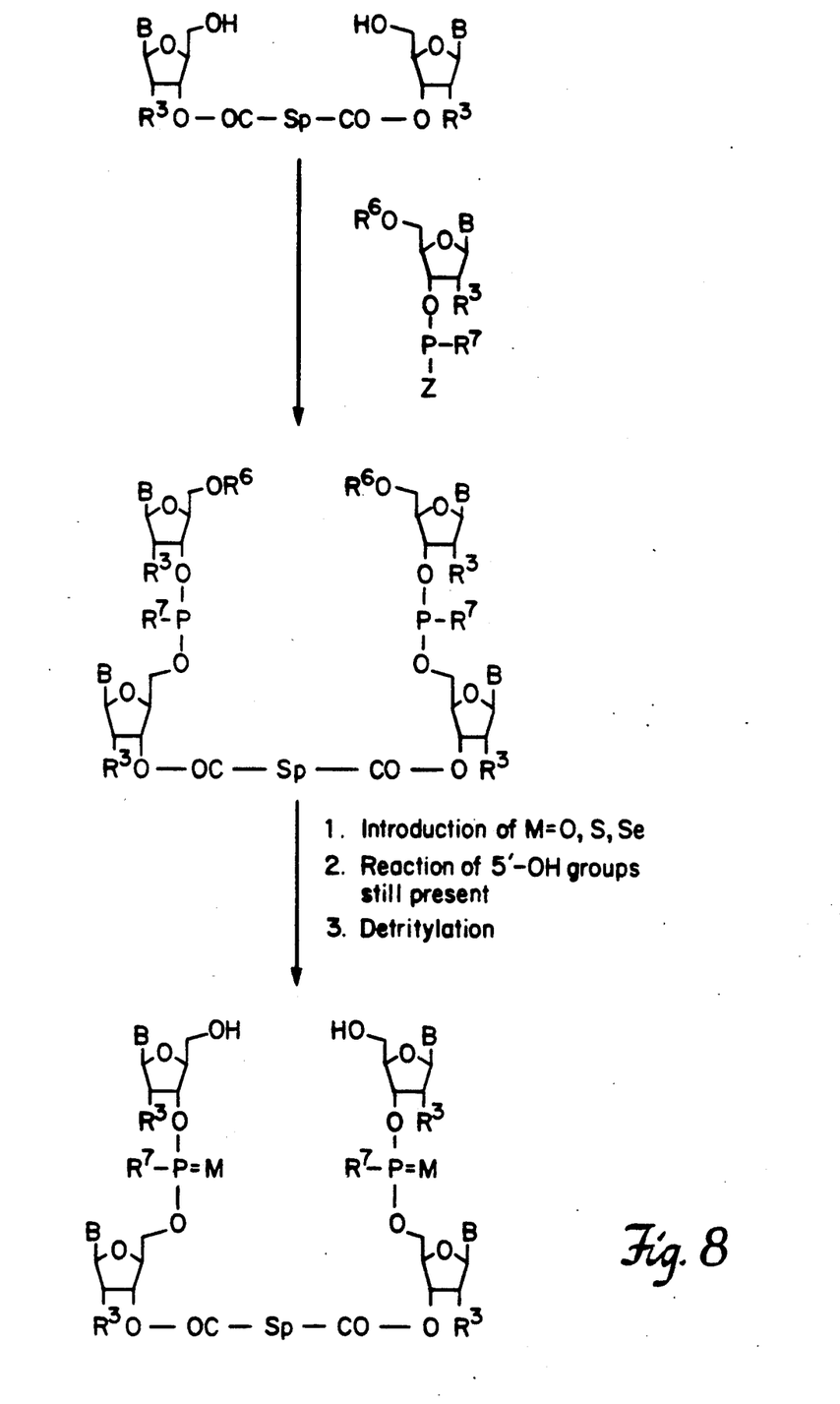

The synthesis of oligophosphonates using a carrier molecule of type A is shown by way of example in FIG. 7, and that using a carrier molecule of type B is shown by way of example in FIG. 8.

Figure 9A:
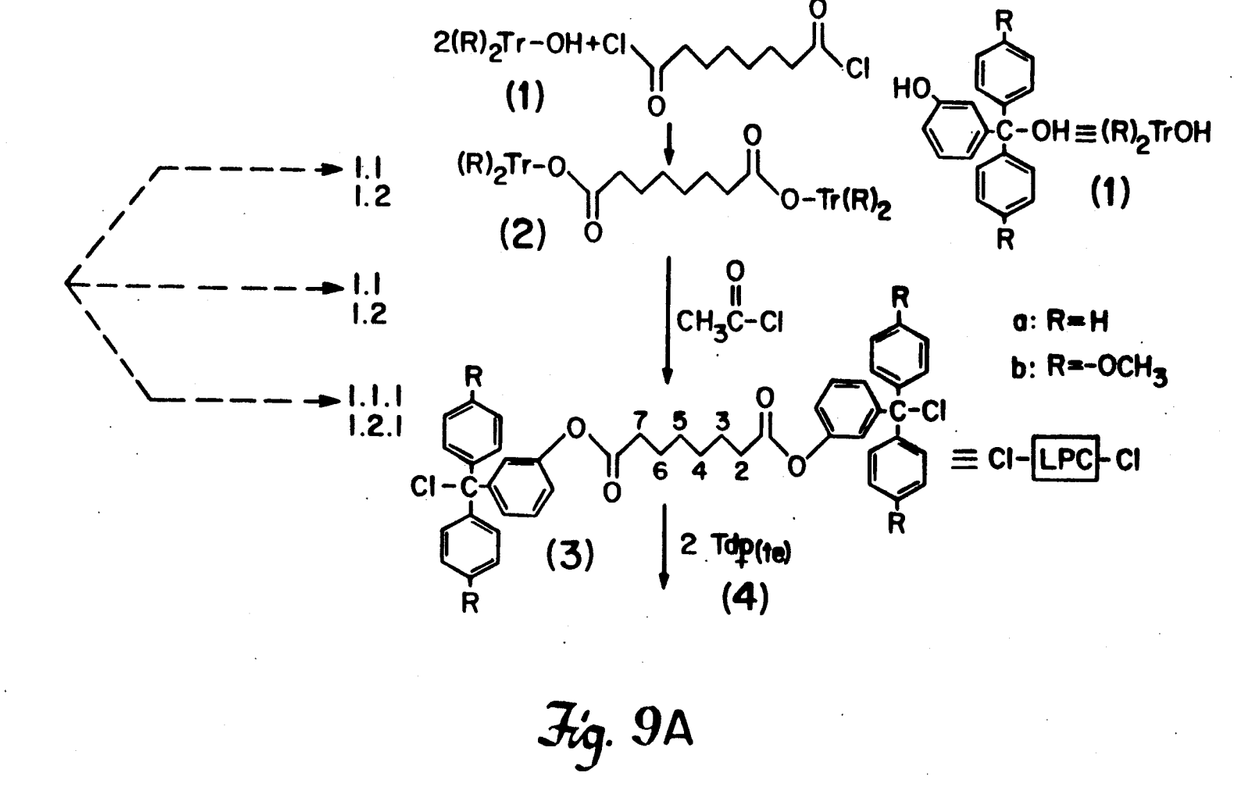
Figure 9B:
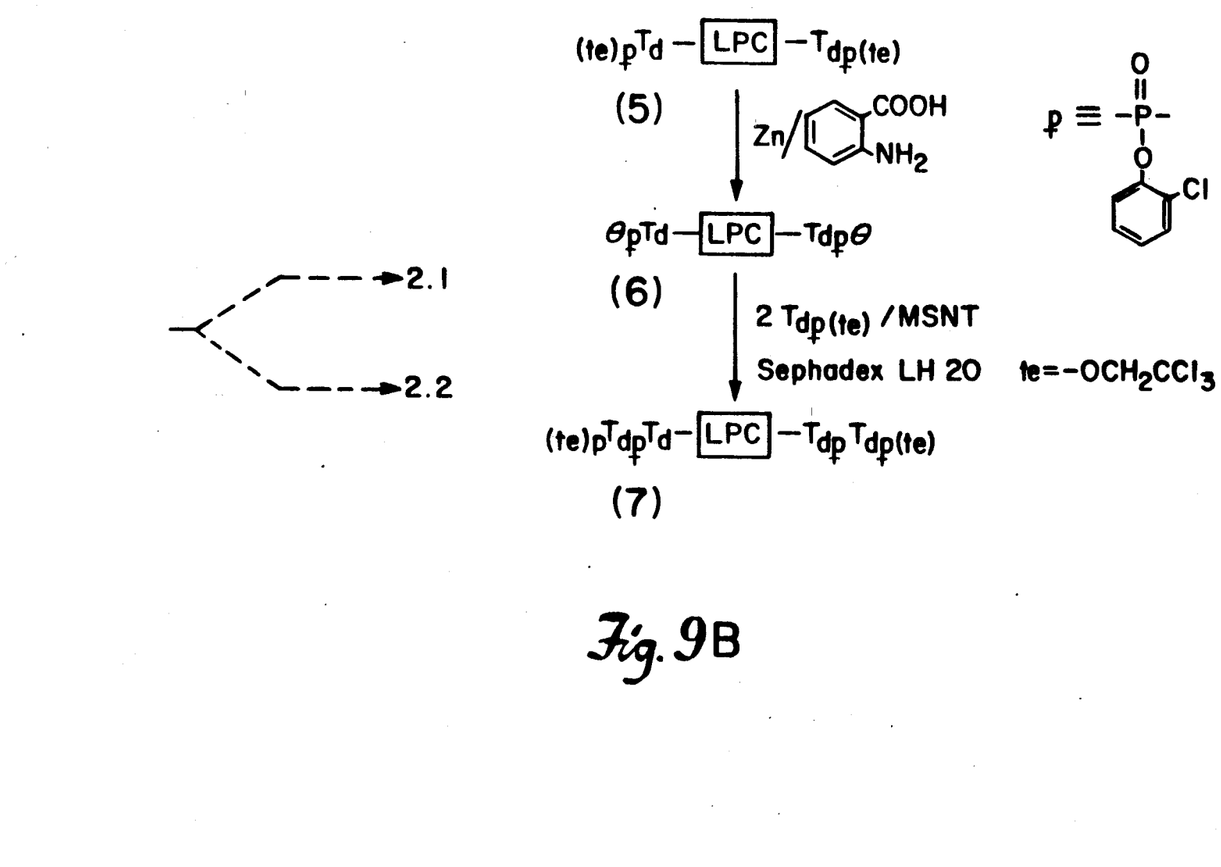
Figure 9C:
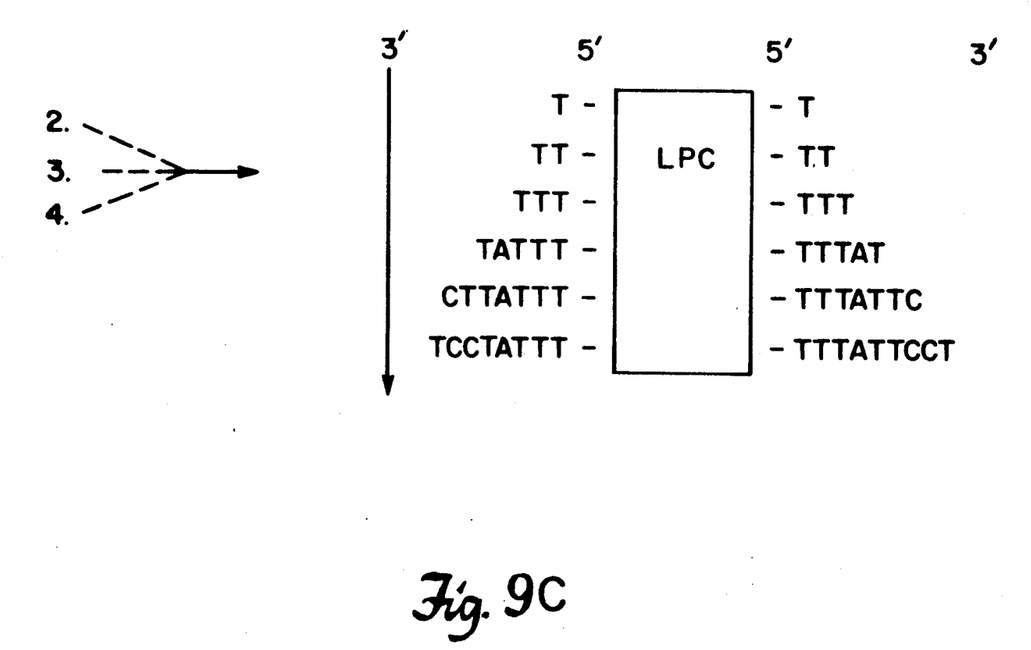

The process according to the invention is illustrated in more detail below with the aid of the synthesis of the oligonucleotides d(TTTATT) and d(TTTATTCCT). The synthesis strategy used in these examples is shown in FIGS. 9A-C; the composition of the starting substances and intermediates can also be seen from these Figures. A survey of other process features of the condensation reactions according to the examples is to be found in Table 1.

In FIGS. 9A-C, the abbreviation LPC ("liquid phase carrier") is used for the carrier molecule, instead of the abbreviation Sp.

EMBODIMENT EXAMPLES

Synthesis of the oligodeoxynucleotides d(TTTAT) and d(TTTATTCCT) on an LPC carrier
1. Preparation of the "liquid phase carrier" (LPC)
 1.1 Suberic acid bridge, anchored via an ester bond to trityl groups
  1.1.1 Tritylation
 1.2 Suberic acid bridge, anchored via an ester bond to dimethoxytrityl groups
  1.2.1 Tritylation
2. Elongation cycle
 2.1 Splitting off of the 3'-terminal trichloroethyl group
 2.2 Condensation reaction with a mono- or dimer-OH (sic) component
 2.3 Gel filtration on Sephadex LH 20
3. De-protection reactions
 3.1 Oximate
 3.2 Concentrated $NH_3$
 3.3 80% strength $CH_3COOH$
4. Anion exchange chromatography on DEAE cellulose
5. Sequencing
 1.1 Preparation of dicarboxylic acid esters (2a) from suberyl chloride (1a)

About 0.4 mmol of suberyl chloride is carefully added to 10 mmol of the alcohol (1a) in 20 ml of pyridine, while cooling with ice and stirring. The batch is then left to stand overnight at room temperature. It is subsequently poured into ice-water, and saturated bicarbonate solution (1:1) is added. After three extractions with 50 ml of $CHCl_3$, the collected $CHCl_3$ phase is dried with $Na_2SO_4$, filtered and concentrated. Final purification on silica gel 60 H. The elution was carried out with pure $CHCl_3$. After concentration of the fractions containing the desired product, the product was precipitated in petroleum ether. Yield: 70%.

Melting point 127° C.

Elemental analysis calculated: C 79.97; H 6.13. Found: C 79.04; H 6.22.

PMR/$CD_3$=D/ 1.38/multiplet, 4 H, 4,4'-H 5,5'-H/, 1.71/multiplet, 4H, 3,3'-H 6,6'-H/, 2.49/t, 4 H, 2,2'-H 7,7'-H/, 6.86–7.26/multiplet, 28 trityl H/.

IR/KBr/: 1740 $cm^{-1}$: —O—C=O; 3550 $cm^{-1}$: —C—OH.

Preparation of the trityl chloride 3a by boiling 2a in toluene/acetyl chloride 1 ml of freshly distilled acetyl chloride was added to a suspension of 3.168 mmol of (2a) in 66 ml of anhydrous toluene and the mixture was boiled under reflux for 6 hours, a further 1.5 ml of acetyl chloride being added after 1 hour. The batch is concentrated under a waterpump vacuum. The residue is taken up in 40 ml of ethyl acetate and the mixture is boiled under reflux and left to stand for slow crystallization. The crystals are filtered off and washed with ethyl ether. Yield: 90%. Melting point 145° C.

Elemental analysis: calculated: C 75.92%; H 5.54%; hydrolyzable Cl 9.74%; Found: C 76.33%; H 5.80%; hydrolyzable Cl 9.72%.

1.1.1 Preparation of completely protected "monomeric LPC derivatives" (5a) - tritylation of thymidine 3'-(2-chlorophenyl-2,2,2-trichloroethyl)-phosphate (4)

2.75 mmol of $T_dP(te)$ (4) are dissolved in 5 ml of absolute pyridine, the solution is concentrated and the residue is dissolved again in 3 ml of absolute pyridine. 1.16 mmol of the dichloride (3a) are dissolved in 4 ml of absolute pyridine and the solution is added to solution 4. The batch is then heated at 100° C in an oil bath for 3.5 hours and the reaction is monitored by thin-layer chromatography using the eluant $CHCl_3$/MeOH (95:5). The reaction is discontinued by addition of EtOH, the mixture is concentrated several times with toluene $CHCl_3$ (3:7) and concentrated to a foam or sirup under gentle conditions under a waterpump vacuum and high vacuum at 30° C. Final purification is by chromatography with 50 g of silica gel per gram of material to be purified. Elution with $CHCl_3$, containing 0–5% of MeOH.

After concentration, the substance thus purified is dissolved in 5 ml of dioxane and freeze-dried. Yield: 44%.

1.2 Preparation of 3-hydroxy-4,4-dimethoxytriphenylcarbinol (1b)

A. Preparation of the Grignard compound 200 ml of THF (absolute) are poured over 2 mol of magnesium chips in a 2 liter three-necked flask with a dropping funnel, stirrer and reflux condenser with a calcium chloride tube, and about one twentieth of a total of 2 mol (12.5 ml) of aryl halide (4-bromoanisole) is added, with stirring.

The start-up of the reaction is noted by the appearance of a slight turbidity and warming of the ether. Should the reaction not start, 0.5 ml of bromine or a few drops of carbon tetrachloride are added to the reaction mixture and the mixture is warmed slightly. After the start-up, the remaining aryl halide is dissolved (235 ml of 4-bromoanisole in 500 ml of THF) and is added dropwise, with further stirring, such that the ether simmers. If the reaction becomes too vigorous, the flask is cooled with water. Towards the end of the dropwise addition, the mixture is simmered on a waterbath until virtually all of the magnesium has dissolved (about 30 minutes).

B. Reaction of the Grignard compound with the carboxylic acid ester 0.6 mol of methyl 3-hydroxybenzoate in 200 ml of absolute THF is added dropwise to the Grignard reagent solution of 2.0 mol of halide (4-bromoanisole), with stirring. When the addition has ended, the mixture is heated for a further 2 hours, with stirring, cooled, and hydrolyzed by addition of 100–150 g of crushed ice, and half-concentrated hydrochloric acid is then added in an amount such that the precipitate formed just dissolves. The reaction mixture is then extracted by shaking 3 times with 300 ml of ethyl ether. The ethereal layer is removed and the aqueous phase is extracted twice more with ether. The combined extracts are washed with saturated bicarbonate solution and a little water. After drying over sodium sulfate, the ether is dissolved off. Thin-layer chromatography (TLC) using the eluant $CHCl_3$/MeOH (95:5) showed the desired product and a product which runs more rapidly and is esterified on the 3-OH group. The batch was therefore taken up in 200 ml of pyridine, 400 ml of concentrated $NH_3$ were added, the suspension was left to stand overnight, with stirring, and concentrated (high vacuum) and the residue was taken up in pyridine (370 ml). This solution is used for the next step.

Preparation of dicarboxylic acid esters (2b) from suberyl chloride and (1b)

0.28 mol of (1b), dissolved in 205 ml of pyridine, is concentrated under a high vacuum, and about 0.112 mol of suberyl chloride in 105 ml of pyridine is carefully added, while cooling with ice and stirring. The batch is then left to stand overnight at room temperature and is concentrated under a high vacuum (oil pump) and the residue is taken up in 200 ml of $CHCl_3$. After three extractions with 150 ml of saturated $NaHCO_3/H_2O$ (1:1), the $CHCl_3$ phase is dried with $Na_2SO_4$, filtered and concentrated. Final purification is carried out by silica gel chromatography. Elution with pure $CHCl_3$. The fractions containing the desired product are further processed directly.

Preparation of the trityl chloride 3b by boiling 2b in toluene/acetyl chloride 10 ml of acetyl chloride are added to a suspension of 5 mmol of (2b) in 40 ml of anhydrous toluene and the mixture is boiled under reflux for 4.5 hours, a further 5 ml of acetyl chloride being added after 1 hour. The batch is concentrated under a waterpump vacuum, the residue is taken up in ethyl acetate and the mixture is kept at 0° C.

1.2.1 Preparation of completely protected "monomeric LPC derivatives" (5b) - tritylation of 4 and 3b in the presence of a molecular sieve powder 5 mmol of the $T_d$ derivative (4) to be tritylated are dissolved in 8.5 ml of pyridine, the solution is concentrated and the residue is dissolved again in 4.0 ml of pyridine. 20 ml of $CH_2Cl_2$ are then added.

After addition of 6 g of freshly activated powdered molecular sieve (4 Å), stirring for 30 minutes and addition of 2.5 mmol of (2b) in 3.5 ml of pyridine, the reaction mixture is stirred overnight and is examined by thin-layer chromatography using the eluant $CHCl_3$/MeOH (95:5).

The reaction is interrupted by addition of 10 ml of EtOH, the molecular sieve is filtered off and rinsed with $CHCl_3$, the filtrate is washed twice with 50 ml of $H_2O$ and the $CHCl_3$ phase is dried with $Na_2SO_4$, filtered and concentrated carefully to a foam or sirup under a waterpump vacuum and high vacuum at 30° C.

Final purification is effected by silica gel chromatography with 50 g of silica gel per gram of material to be purified. Elution with $CHCl_3$ containing 2% of MeOH. After concentration of the solvent, the substance thus purified is dissolved in dioxane and freeze-dried. Yield: 71%

2. Elongation cycle 2.1 Stripping off of the 3'-terminal trichloroethyl group

Per mmol of triester in 15–20 ml of pyridine, anthranilic acid (10 equivalents) and activated zinc powder (10 equivalents) are added successively, with magnetic stirring. The reaction is monitored by thin-layer chromatography using the eluant $CHCl_3$/MeOH (9:1) and (6:4). After 30 minutes, a mixture of $H_2O$/triethylamine/pyridine (0.3/0.625/1) is added. After a further 10 minutes of stirring, the mixture is filtered off from the zinc over a glass frit directly into a separating funnel containing 125 ml of saturated $NaHCO_3$ solution, rinsed with 10 ml of pyridine and extracted with four 50 ml portions of chloroform and the organic phase is collected and washed three times with 50 ml of saturated $NaHCO_3$ solution. After re-extraction of the aqueous phase with 50 ml of chloroform, the organic phase is dried with $Na_2SO_4$, filtered and concentrated.

In the case of compound (5b), the final prification is carried out on an RP 2 column with the eluting agent MeOH/$H_2O$ (8:2). In the case of larger molecules, the purified LPC oligonucleotide 3'-phosphoric acid diester is used directly for the condensation.

2.2 Condensation reaction with monomeric or dimeric OH components

OH components (three-fold excess over the LPC phosphate component) and LPC phosphate components are coevaporated twice to a foam and once to about half the volume with in each case 10 ml of pyridine per mmol of phosphate component for the purpose of azeotropic drying, 4.5–5 equivalents of 1-(mesitylene-2-sulfonyl)-3-nitro-1,2,4-triazole (MSNT) are added and the mixture is stirred magnetically for 1–5 hours, depending on the chain length, whilst being monitored by TLC. To discontinue the reaction, 1.5 ml of saturated $NaHCO_3$ solution are added to the batch and the mixture is transferred to a separating funnel containing 75 ml of saturated $NaHCO_3$ solution by means of 50 ml of CHCl₃. After six extractions with in each case 30 ml of CHCl₃, the collected CHCl₃ phase is dried with Na₂SO₄, filtered and concentrated. Final purification on Sephadex LH 20.

2.3 Gel filtration on Sephadex LH 20

The final purification of the reaction mixture following the condensation reaction is carried out on Sephadex LH 20 with the eluant CHCl₃/EtOH (7:3). A column of 63×3.6 cm (640 cm³, exclusion volume 200 ml) is used. Flow rate 120 ml/hour, fractions of 2 ml each.

The constituents of the condensation reaction mixture are eluted in the following sequence: condensation products (fractions 1–20), unreacted phosphate component (15–35), sulfonylated OH component (30–50), unreacted OH component (40–75).

Only in the case of longer chains, where relatively large LPC phosphate components have been used for the condensation reaction, can overlapping occasionally be observed between unreacted LPC phosphate components and condensation products. In these cases, filtration was carried out over a very thin layer of silica gel, 60 H (Merck).

3. De-protection reactions

Hexameric TTTATT is filtered over silica gel, after Sephadex LH 20 chromatography.

Nonameric TTTATTCCT is purified, after Sephadex LH 20 chromatography, by thin-layer chromatography on RP-18 in the eluant acetone/H₂O (75:25).

3.1 Splitting off of the phosphate-protective groups with oximate

The purified material is dissolved in 200 μl of dioxane and 0.2 mmol of pyridine-2-carboxaldoxime (24.4 mg), 0.2 mmol of tetramethylguanidine (25 μl) and 200 μl of water are added. After 24 hours, a further 0.2 mmol of tetramethylguanidine is added, and the mixture is reacted at room temperature for a further 26 hours.

3.2 Splitting off of the N- and O-protective groups with concentrated NH₃

0.85 ml of concentrated aqueous NH₃ is then added to the mixture and the resulting homogeneous solution is sealed tightly, kept at 50° C for 24 hours and concentrated under mild conditions.

3.3 Splitting of the trityl ether bond with 80% strength CH₃COOH

The material thus obtained is taken up in 1 ml of 80% strength acetic acid and is kept at room temperature for 2.5 hours. It is then concentrated by freeze-drying, the residue is dissolved in 400 μl of H₂O and the solution is extracted with CHCl₃. The aqueous phase is neutralized with NH₃. The mixture thus obtained is diluted with 10 ml of 25 mmol tris.HCl buffer (pH 7.5)/7M urea. Final purification is effected by DEAE-cellulose/anion exchange chromatography.

4. Anion exchange chromatography on DEAE-cellulose

The de-protected material is absorbed from dilute solution onto a DEAE-cellulose column (12 cm long, 21 cm³ capacity) equilibrated with 25 mmol of tris.HCl buffer (pH 7.5)/7M urea. The material is then washed thoroughly with 50 mM NaCl in the same buffer and eluted with an ionic strength gradient from 50 mmol to 500 mmol of NaCl, also in the same buffer. The hexanucleotide is eluted at an NaCl concentration of about 0.225 mmol of NaCl. The nonanucleotide was eluted at an NaCl concentration of about 0.285 mmol of NaCl.

5. Sequence analysis

The sequence analysis then carried out was effected by the "mobility shift method".

Bibliography

F. Sanger et al., PNAS 70, 1209 (1973).

E. Jay et al., NAR 1, 331–52 (1974).

H. Blöcker and H. Köster, Liebigs Ann. Chem. 1978, 982–90.

Equation 1

TABLE 1

| | | CONDENSATION REACTIONS | | | | |
| | | OH Component | | | MSNT | Condensation yield |
| Phosphate component | (mmol) | | (mmol) | n | (mmol) | Product (%) |
| --- | --- | --- | --- | --- | --- | --- |
| LPC—(Tp⁻)₂ | 1.00 | Tp(te) | 3.00 | 1 | 4.50 | LPC—(TpTp(te))₂ (81) |
| LPC—(TpTp⁻)₂ | 0.57 | Tp(te) | 1.72 | 1 | 2.60 | LPC—(TpTpTp(te))₂ (57.5) |
| LPC—(TpTpTp⁻)₂ | 0.37 | A^bzpTp(te) | 0.62 | 1 | 1.67 | LPC—(TpTpTpA^bzpTp(te))₂ (30) |
| LPC—(TpTpTpA^bzTp⁻)₂ | 0.04 | TpC^tlp(te) | 0.10 | 2 | 0.20 | LPC—(TpTpTpA^bzpTpTpC^tlp(te))₂ (35) |
| LPC—(TpTpTpA^bzpTpTpC^tlp⁻)₂ | 0.008 | C^tlpT(Bb) | 0.02 | 5 | 0.04 | LPC—(TpTpTpA^bzpTpTpC^tlpCpT(Bb))₂(—) |
| LPC—(TpTpTpA^bzpTp⁻)₂ | 0.03 | T(Bb) | 0.105 | 4 | 0.15 | LPC—(TpTpTpA^bzpTpT(Bb))₂ (56) | te: 2,2,2-Trichloroethyl
bz: Benzoyl
tl: 2-Toluyl
Bb: 4-tert-butylbenzoyl

I claim:

1. A process of preparing oligonucleotides in a liquid phase reaction mixture, comprising the steps of:
   a) reacting a bifunctional carrier molecule, which is soluble in, and chromatographically separable from, the reaction mixture, the carrier molecule having the formula:

wherein:
(i) n is an integer from 2 to 10; and
(ii) X is a trityl halide;

with at least an equimolar amount of a first nucleoside, nucleotide, or oligonucleotide, $N^1$;

b) separating and purifying the compound formed by the reaction in step (a) by chromatography, said compound having the formula:

$$N^1-X-O-\overset{\overset{O}{\|}}{C}(CH_2)_n\overset{\overset{O}{\|}}{C}-O-X-N^1;$$

c) repeating steps (a) and (b) to add additional nucleotides $N^2 \ldots N^m$ to form an oligonucleotide having the formula:

$$N^m \ldots N^1-X-O-\overset{O}{C}(CH_2)_n\overset{O}{C}-O-X-N^1 \ldots N^m$$

wherein m is an integer from 3 to 50 and wherein the oligonucleotide is soluble in and chromatographically separable from the reaction mixture; and d) releasing the oligonucleotide from the carrier molecule by contacting said oligonucleotide with acetic acid, thereby obtaining an oligonucleotide having the formula:

$$N^1, N^2 \ldots N^m.$$

2. A process of claim 1, wherein n is 6.

3. A process of claim 2, wherein X is dimethoxytrityl chloride.

4. A process of preparing oligonucleotides in a liquid phase reaction mixture comprising the steps of:

a) reacting a carrier molecule having the formula:

wherein R is —OCH$_3$, with at least an equimolar amount of a nucleoside or nucleotide;

b) separating and purifying the compound formed in (a) by gel filtration chromatography c) repeating steps (a) and (b) to form an oligonucleotide which is chromatographably separable from the reaction mixture; and d) releasing the oligonucleotide from the carrier molecule by contacting said oligonucleotide with acetic acid.

5. A process of claim 4, wherein the nucleoside, nucleotide or oligonucleotide is protected.

6. A process of claim 4, wherein the oligonucleotide contains from about 3 to about 50 nucleotide bases.

7. A process of claim 4, wherein the carrier molecule is soluble in the liquid phase reaction mixture.

8. A process of claim 4 further comprising the step of releasing the oligonucleotides from the carrier molecule by contacting said oligonucleotides with acetic acid.

* * * * *